United States Patent [19]

Youssef

[11] 4,248,971

[45] Feb. 3, 1981

[54] INSTANT CULTURE MEDIA AND METHOD OF STERILIZING SAME

[76] Inventor: Kamal A. Youssef, P.O. Box 6548, W. Palm Beach, Fla.

[21] Appl. No.: 913,584

[22] Filed: Jun. 8, 1978

[51] Int. Cl.$^3$ .............................................. C12N 1/20
[52] U.S. Cl. ..................... 435/253; 422/28; 422/30; 422/37; 435/243; 435/254; 435/255; 435/256; 435/800
[58] Field of Search ................. 195/99, 100, 101, 102, 195/109, 123, 104, 108, 126; 422/28, 30, 34, 36, 37; 252/401, 399, 405, 407; 435/243, 253, 254, 255, 256, 800

[56] References Cited

U.S. PATENT DOCUMENTS

| 620,022 | 2/1899 | Effront | 195/123 X |
|---|---|---|---|
| 2,189,949 | 2/1940 | Griffith et al. | 422/34 |
| 3,041,250 | 6/1962 | Wolnak et al. | 195/123 X |
| 3,293,145 | 12/1966 | Leavitt et al. | 195/100 X |
| 4,040,977 | 8/1977 | Eggensperger et al. | 252/401 |

FOREIGN PATENT DOCUMENTS 266414  2/1927  United Kingdom ................. 435/800

OTHER PUBLICATIONS

Martin Frobisher, Fundamentals of Microbiology, 8th Ed. W. B. Saunders Company; 1970 p. 41.

*Primary Examiner*—Robert J. Warden
*Attorney, Agent, or Firm*—Albert F. Kronman

[57] ABSTRACT

Disclosed are culture media comprising an aqueous solution of a gelling agent, a compound such as a bleach capable of sterilizing the gelling agent and its container.

Also disclosed is a method for sterilizing a culture medium without autoclaving same by dissolving a gelling agent in boiling water; adding cool water to the aqueous gelling agent solution; dissolving a sterilizing agent in the cooled solution adding nutrients and then growing the culture.

6 Claims, No Drawings

INSTANT CULTURE MEDIA AND METHOD OF STERILIZING SAME

FIELD OF THE INVENTION

This invention relates to an instant culture medium which I call the "Instant A-B-C Culture Medium" and to a method for sterilizing culture media without autoclaving.

BACKGROUND OF THE INVENTION

The standard routine practice in the vast majority of laboratories is to sterilize the microbiological and bacteriological culture media by the heating process called "autoclaving". Autoclaving is a form of "pressure-cooking" by which the nutrients or media are subjected to "trapped" or pressurized steam in a sturdy vessel "autoclave" or "pressure cooker" usually under a pressure of 15 lb/square inch to produce a temperature of approximately 121° C. for about 20 minutes exposure of the medium to this "superheated steam" ensures or guarantees the destruction or annihilation of all forms of life: vegetative and otherwise (e.g. heat-resistant spores). The drawbacks or disadvantages of this widely used method of sterilizing culture media, include:

1. Caramelization.
2. pH Changes
3. Protein desintegration, denaturation and/or breakdown.
4. Inactivation of certain vitamins and growth-promoting factors.
5. Clouding and adverse effects on the optical clarity of the medium.
6. Possible undesirable physical and/or chemical actions and interactions that may take place by and among the different ingredients of the medium
7. Agar agar hydrolysis
8. Frequency of failures, errors, hazards and accidents related to heat sterilization equipment i.e. the autoclave.
9. Time consuming There is accordingly a need for a culture medium which will obviate the aforementioned drawbacks of the prior art and which will have a long shelf life.

The main object of this invention is to provide such a medium.

SUMMARY OF THE INVENTION

Culture media in accordance with the present invention comprise in weight percent:
   from 0.1% to 4% of a gelling agent;
   from 0.015% to 0.03% of a sterilizing agent
   from 7% to 50% of a nutrient concentrate, preferably, cold concentrated nutrients. The preferred amount is from 7 to 14% and a more preferred amount ranges from 7 to 10%.

More specifically, the media comprises: "A"—Agar agar: or One or more similar jelling agent/s such as Carrageenan, pectin, silica gel, etc. "B"—comprises one ore more of several substances or compounds which when exposed to a solution of "A" would effectively sterilize (through the evolution of a sterilizing gas or "fumes" e.g. chlorine or ethylene oxide) the container and the solution contained therein instantly. Examples of such substances are:

Bleaching agents and liquids, such as hypochlorites and hypochlorous acid and its salts, hypobromites, hypobromic acid, and its salts, hyposulfites and sulfurous acid and its salts, chlorine, bromine and halogen liberating compounds both inorganic and organic such as sodium dichloro-s-triazinetrione dihydrate sodium dichloro-isocyanurate dihydrate), trichloro-s-triazinetrione or trichloroisocyanuric acid (which may contain more than thirty-nine percent available chlorine). Oxygen bleach such as sodium perborate, perboric acid, hydrogen peroxide, formaldehyde, formamides, ketones, aldehydes, volatile acids and alkalies, volatile acids, ketones and aldehyde liberating compounds, chloroform, acetone, ethylene oxide, ethylene oxide gas or solution and ethylene-oxide liberating compound and other sterilizing gas-liberating-compounds. "C"—Concentrate-This is typically a ten to fifteen times concentrated aqueous solution or powder of the "nitrients" and/or "active ingredients" cold-sterilized by micro-filtration through a 0.2 micron filter and typically dispensed in clear sterile glass containers in known and predetermined amounts e.g. 50 cc., 10 cc, 250 cc., and 500 cc., or 25 g, 50 g. etc. It is also realized that certain components or active ingredients may be naturally sterile and may not need sterilization, such as chloroform or alcohol in appropriate concentrations.

The culture sterilizing method of this invention comprises the steps of: dissolving from 0.1% to 4% parts by weight of a gelling agent in boiling pure (not necessarily sterile) or clear tap water; agitating the container and continuing to boil for 2–3 minutes or until the solution becomes uniform and clear then adding sufficient water at a temperature of between 15° C. and 25° C. to bring the solution to the desired quantity being proposed, adding from 0.015% to 0.03% by weight of the sterilizing agent to the solution, loosely closing the container, agitating until all the solids have dissolved, and then adding the nutrient concentrate in an amount ranging from 7% to 10% parts by weight. The medium temperature is controlled by bringing it down to a temperature of about 45 degrees celcius. The culture medium is then poured into sterile containers and allowed to cool to room temperature. It is then ready for use.

The invention is further illustrated in non-limiting fashion by the following examples.

EXAMPLE I

This preparation requires the following equipment:
   Two clean and dry two-liter capacity Pyrex (or equivalent quality) graduated conical flasks (Erlenmeyer's flasks) marked 1 and 2 and loosely capped e.g. with heavy-duty aluminum foil.
   Bunsen burner or electric hot plate.
   Fifty to sixty clean, dry and sterile Petri dishes
   One pair of mitts or oven gauntlets

TO PREPARE THE CULTURE MEDIUM

Boil 400 c.c. of pure water (not necessarily sterile) or clear tap water in flask marked "1". Empty the contents (agar) of packet "A" described below in flask marked "2". Add gradually the briskly boiling water, shaking vigorously meanwhile to insure uniform suspension and melting of the agar. Bring to a boil on a strong direct flame with gentle shaking of the flask. Add 600 c.c. cool pure water (not necessarily sterile) or clear tap water to the agar solution gradually with vigorous shaking to insure uniform agar solution without any residues on the flask wall. Now, empty the contents of Packet "B" described below, onto the agar solution and promptly recap the flask and shake vigorously until all the added ingredients completely dissolve. With sterile precautions add the contents of the packet "C" described below to the now "sterile" agar solution. Shake vigorously to mix thoroughly the nutrients (active ingredients). Pour into sterile containers. The media is then ready to use as soon as it reaches room temperature and can be poured on a Petri dish.

EXAMPLE II

By proceeding as in Example I, there is prepared an Instant A-B-C Blood Culture Medium.

Agar (Tryptic Soy base). To make approximately 1000 c.c. of the medium mix:

| Packet "A" (of A, B, and C) | |
|---|---|
| Agar agar | 15.00 Gram |
| Packet "B" (of A, B, and C) | |
| Sod. Dichloro-s-Triazinetrione Dihydrate | 0.20 Gram |
| Buffering and/or Osmo-Stabilizers (to prevent the hemolysis of blood, if added) | 3.50 Gram |
| Packet "C" (of A, B, and C) (100 c.c. Bottle) | |
| Casein digest | 17.00 Gram |
| Soy bean digest | 3.00 Gram |
| Dipotassium phosphate | 2.00 Gram |
| Dextrose | 2.00 Gram |
| Sulfhydryl compound | 0.50 Gram |
| (British Anti Lewisite (B.A.L.) or sod. thioglycollate to inactivate residual chlorine (if any). | |

EXAMPLE III

Proceeding as in Example I, there is prepared an

| Instant Mueller-Hinton Medium For Antibiotic Sensitivity Tests By The Kirby Bauer Method | |
|---|---|
| To make 100 c.c. mix: | |
| Packet "A" (of A, B & C) | |
| Agar agar | 15.00 Gram |
| Packet "B" (of A, B & C) | |
| Sod. Dichloro-s-Triazinetrione dihydrate | 0.20 Gram |
| Buffering &/or Osmo-stabilizers (to allow the addition of blood if necessary | 1.00 Gram |
| Packet "C" (of A, B & C) (100 c.c. bottle) | |
| Beef infusion from | 300.00 Gram |
| Acid digested casein | 17.50 Gram |
| Starch | 1.50 Gram |
| Sulfhydryl compound (B.A.L. or sodium thiogylycollate) | 0.50 Gram |

EXAMPLE IV

Proceeding as in Example I, there is prepared an

| Instant G-C Medium (for Gonococcus) | |
|---|---|
| To make 1000 c.c., mix: Packet "A" (of A, B & C) | |
| Agar agar | 12.50 Gram |
| Packet "B" (of A, B & C) | |
| Sol. Dichloro-s-Triazinetrione dihydrate | 0.20 Gram |
| Buffering &/or Osmo-Stabilizers (to protect against hemolysis if blood is added) | 3.50 Gram |
| Packet "C" (of A, B & C) | |
| Peptone (meat digest) | 10.00 Gram |
| Liver extract | 3.00 Gram |
| Yeast extract | 3.00 Gram |
| Corn starch | 1.00 Gram |
| Dextrose | 2.00 Gram |
| Dipotassium phosphate | 2.00 Gram |
| Sulfhydryl compound (B.A.L. or Thio) | 0.50 Gram |

The medium of this invention is instantly ready to pour or if desired, 50 c.c. of fresh and sterile defibrinated sheep or horse blood can be added taking sterile precautions, mixed well and the nutrient blood agar medium is ready for pouring. There is no need to wait for the medium to cool, as its temperature is already controlled.

The medium typically sets (solidifies) promptly, because of the controlled temperature of the medium and there will be no excessive moisture on the lid or walls of the containers (Petri dishes or tubes, etc.) and the surface of the medium is bubblefree. The medium will grow distinctly better all microorganisms that grow on blood agar with the highest recovery rate attainable and with the eariest to read reactions e.g. hemolysis, morphology, size of the colonies, etc. All the above mentioned drawbacks inherent in heat sterilization are completely avoided.

The medium of the invention has been thoroughly tested under actual use conditions and has been found to be completely successful for the accomplishment of the above stated objects of the invention.

The present invention has been disclosed herein with particular respect to certain preferred embodiments thereof. However, a latitude of modification, change and substitution is intended in the foregoing disclosure, and in some instances some components of the invention will be employed with certain other components for optimum results. Accordingly, other compositions encompassed by the above disclosure are fully equivalent to those claimed hereinbelow.

What is claimed is:

1. A culture medium comprising: from about 0.1 to about 4.0 percent of a gelling agent selected from the group consisting of agar agar, pectin, silica gel and carageenan; from about 0.015 to about 0.03 weight percent of at least one halogen-liberating sterilizing compound compatible with said gelling agent and capable of sterilizing said gelling agent in aqueous medium; and from about 7 to about 50 weight percent of nutrients.

2. The medium of claim 1, wherein said gelling agent, said sterilizing compound and said nutrients are provided in separate additive packages.

3. The medium of claim 1, wherein said sterilizing compound is sodium dichloro-s-triazinetrione dihydrate, sodium dichloro-isocyanurate dihydrate, trichloro-s-triazinetrione or trichloroisocyanuric acid.

4. The method for forming and sterilizing a culture medium which comprises the steps of: dissolving from about 0.1 to about 4.0 percent by weight of a gelling agent in boiling water then adding cooler water at a temperature ranging from 15° to 25° C. to the resulting solution; mixing with the cooled solution from about 0.015 to 0.03 percent by weight of at least one halogen-liberating sterilizing compound compatible with said gelling agent and having a sterilizing effect thereon, said gelling agent being selected from the group of agar agar, pectin silica gel and carageenan; and adding from 7.0 to about 50 percent by weight of a concentrated solution of nutrients; pouring the culture to be grown into suitable sterile containers and cooling to room temperature.

5. The method of claim 4 wherein said solution after adding of said cooler water is brought to a temperature of about 45 degrees C.

6. The method of claim 4, wherein said sterilizing compound is sodium dichloro-s-triazinetrione dihydrate, sodium dichloro-isocyanurate dihydrate, trichloro-s-triazinetrione or trichloroisocyanuric acid.

* * * * *